(12) United States Patent
He et al.

(10) Patent No.: US 6,920,282 B2
(45) Date of Patent: Jul. 19, 2005

(54) METHODS AND APPARATUS FOR A CONTROLLABLE VAPOR-DISPENSING DEVICE

(75) Inventors: Mengtao Pete He, Scottsdale, AZ (US);
Carl Triplett, Scottsdale, AZ (US);
Mary Conway, Phoenix, AZ (US);
David Rinaldis, Longmont, CO (US);
Michael Strasser, Boulder, CO (US);
Francis Joseph Mills, IV, Holt, MI (US)

(73) Assignee: The Dial Corporation, Scottsdale, AZ (US)

( * ) Notice: Subject to any disclaimer, the term of this patent is extended or adjusted under 35 U.S.C. 154(b) by 0 days.

(21) Appl. No.: 10/640,141

(22) Filed: Aug. 13, 2003

(65) Prior Publication Data

US 2004/0105669 A1 Jun. 3, 2004

Related U.S. Application Data

(63) Continuation-in-part of application No. 10/222,500, filed on Aug. 16, 2002.

(51) Int. Cl.$^7$ ................................................ F24F 6/08
(52) U.S. Cl. ...................................... 392/392; 392/395
(58) Field of Search .............................. 392/390, 392, 392/397, 396; 261/94, 99, DIG. 65; 239/34, 29, 25

(56) References Cited

U.S. PATENT DOCUMENTS

| | | | |
|---|---|---|---|
| 1,836,600 A | 12/1931 | Jones | |
| 3,262,290 A | * 7/1966 | Huber | ........................ 431/328 |
| 3,748,438 A | 7/1973 | Costello | |
| 3,780,260 A | 12/1973 | Eisner | |
| 3,895,928 A | 7/1975 | Gonzalo | |
| 3,908,905 A | 9/1975 | Von Philipp et al. | |
| 3,923,458 A | 12/1975 | Gonzalo | |
| 3,948,445 A | 4/1976 | Andweg | |
| 4,017,030 A | 4/1977 | Coplan et al. | |
| 4,037,353 A | 7/1977 | Hennart et al. | |
| 4,084,079 A | 4/1978 | Costello | |
| 4,111,655 A | 9/1978 | Quincey | |
| 4,123,741 A | 10/1978 | Kiyono et al. | |
| 4,165,835 A | 8/1979 | Dearling | |
| 4,171,340 A | 10/1979 | Nishimura et al. | |
| 4,208,012 A | 6/1980 | Dutcher | |
| 4,214,146 A | 7/1980 | Schimanski | |
| 4,220,281 A | 9/1980 | Martens, III et al. | |
| 4,228,124 A | 10/1980 | Kashihara et al. | |
| 4,243,969 A | 1/1981 | Steigerwald et al. | |

(Continued)

FOREIGN PATENT DOCUMENTS

| | | |
|---|---|---|
| DE | 35 35 564 | 5/1986 |
| DE | 41 31 613 | 3/1993 |
| EP | 0 296 807 | 12/1988 |

(Continued)

OTHER PUBLICATIONS

PCT Inernational Search Report issued Dec. 17, 2003 for International Application No. PCT/US03/26511, International Filing Date Aug. 26, 2003, 4 pages.

(Continued)

*Primary Examiner*—Sang Y Paik
(74) *Attorney, Agent, or Firm*—Snell & Wilmer L.L.P.

(57) ABSTRACT

A vapor-dispensing device exhibiting a range of evaporation rates corresponding to a discernable range of sensory fragrance intensity levels. The vapor-delivery device includes one or more control structure (e.g., a heat control, a vent control, and/or the like) configured to allow a user to specify the evaporation rate of the vapor-dispensing device over a continuous or discretized range of values. In accordance with another aspect of the invention, the two extremes of operation correspond to a range of sensory fragrance intensity values that span at least three minimum perceivable intensity zones.

3 Claims, 11 Drawing Sheets

U.S. PATENT DOCUMENTS

| | | |
|---|---|---|
| 4,293,173 A | 10/1981 | Tricca |
| 4,294,778 A | 10/1981 | DeLuca |
| 4,346,059 A | 8/1982 | Spector |
| 4,391,781 A | 7/1983 | Van Lit |
| 4,408,813 A | 10/1983 | Koehler |
| 4,413,779 A | 11/1983 | Santini |
| 4,415,797 A | 11/1983 | Choustoulakis |
| 4,425,302 A | 1/1984 | Pons Pons |
| 4,467,177 A | 8/1984 | Zobele |
| 4,518,212 A | 5/1985 | Rumble |
| 4,530,556 A | 7/1985 | Bonus |
| 4,537,351 A | 8/1985 | Wilson |
| 4,544,592 A | 10/1985 | Spector |
| 4,549,250 A | 10/1985 | Spector |
| 4,556,539 A | 12/1985 | Spector |
| 4,571,485 A | 2/1986 | Spector |
| 4,574,181 A | 3/1986 | Spector |
| 4,595,564 A | 6/1986 | Spector et al. |
| 4,631,387 A | 12/1986 | Glucksman |
| 4,658,985 A | 4/1987 | Madsen et al. |
| 4,660,764 A | 4/1987 | Joyaux et al. |
| 4,662,679 A | 5/1987 | Franck et al. |
| 4,675,504 A | 6/1987 | Suhajda |
| 4,686,353 A | 8/1987 | Spector |
| 4,695,434 A | 9/1987 | Spector |
| 4,703,155 A | 10/1987 | Suhajda |
| 4,707,336 A | 11/1987 | Jones |
| 4,714,984 A | 12/1987 | Spector |
| 4,718,856 A | 1/1988 | Pinkerton et al. |
| 4,725,712 A | 2/1988 | Schroeder |
| 4,731,520 A * | 3/1988 | Glucksman et al. ........ 392/390 |
| 4,731,522 A | 3/1988 | Manchester |
| 4,732,321 A | 3/1988 | Dolan |
| 4,734,560 A | 3/1988 | Bowen |
| 4,739,928 A | 4/1988 | O'Neil |
| 4,743,406 A | 5/1988 | Steiner et al. |
| 4,753,389 A | 6/1988 | Davis |
| 4,777,345 A | 10/1988 | Manchester |
| 4,780,286 A | 10/1988 | Parent et al. |
| 4,795,883 A | 1/1989 | Glucksman et al. |
| 4,798,935 A | 1/1989 | Pezaris |
| 4,800,239 A | 1/1989 | Hill |
| 4,801,271 A | 1/1989 | Piper |
| 4,804,821 A | 2/1989 | Glucksman |
| 4,808,347 A | 2/1989 | Dawn |
| 4,816,973 A | 3/1989 | Atalla et al. |
| 4,830,791 A | 5/1989 | Muderlak et al. |
| 4,837,421 A | 6/1989 | Luthy |
| 4,849,606 A | 7/1989 | Martens, III et al. |
| 4,853,517 A | 8/1989 | Bowen et al. |
| 4,878,615 A | 11/1989 | Losi |
| 4,886,469 A | 12/1989 | Jseng |
| 4,915,301 A | 4/1990 | Munteanu |
| 4,919,981 A | 4/1990 | Levey et al. |
| 4,931,224 A | 6/1990 | Holzner, Sr. |
| 4,931,258 A | 6/1990 | Zlotnik et al. |
| 4,968,456 A | 11/1990 | Muderlak et al. |
| D315,789 S | 3/1991 | Muderlak |
| 4,998,671 A | 3/1991 | Leifheit |
| 5,004,435 A | 4/1991 | Jammet |
| 5,014,913 A | 5/1991 | Hoyt et al. |
| 5,015,442 A | 5/1991 | Hirai |
| 5,029,729 A | 7/1991 | Madsen et al. |
| 5,038,394 A * | 8/1991 | Hasegawa et al. .......... 392/395 |
| 5,050,798 A | 9/1991 | Sullivan |
| 5,106,317 A | 4/1992 | Taylor |
| 5,111,477 A | 5/1992 | Muderlak et al. |
| 5,115,975 A | 5/1992 | Shilling |
| 5,121,881 A | 6/1992 | Lembeck |
| 5,126,078 A | 6/1992 | Steiner et al. |
| 5,136,684 A | 8/1992 | Lonker et al. |
| 5,147,582 A | 9/1992 | Holzner, Sr. et al. |
| 5,148,984 A | 9/1992 | Bryson, Jr. et al. |
| 5,175,791 A | 12/1992 | Muderlak et al. |
| 5,196,171 A | 3/1993 | Peltier |
| 5,201,025 A | 4/1993 | Landesberg |
| 5,217,696 A | 6/1993 | Wolverton et al. |
| 5,220,636 A | 6/1993 | Chang |
| 5,222,186 A | 6/1993 | Schimanski et al. |
| 5,223,182 A | 6/1993 | Steiner et al. |
| 5,233,680 A | 8/1993 | Fussell |
| 5,239,610 A | 8/1993 | Shao |
| 5,240,426 A | 8/1993 | Barla |
| 5,285,014 A | 2/1994 | Gilchrist |
| 5,290,546 A | 3/1994 | Hasegawa et al. |
| 5,295,845 A | 3/1994 | Changxing |
| 5,314,669 A | 5/1994 | Hamilton |
| 5,320,542 A | 6/1994 | Cheng |
| 5,339,065 A | 8/1994 | Slenker |
| 5,342,584 A | 8/1994 | Fritz et al. |
| 5,373,581 A | 12/1994 | Smith |
| 5,375,728 A | 12/1994 | West |
| 5,376,338 A | 12/1994 | Zlotnik |
| 5,382,410 A | 1/1995 | Peltier |
| D355,251 S | 2/1995 | Paulovich et al. |
| 5,394,506 A | 2/1995 | Stein et al. |
| 5,402,517 A | 3/1995 | Gillett et al. |
| D357,330 S | 4/1995 | Wong et al. |
| 5,431,859 A | 7/1995 | Tobin |
| 5,431,885 A | 7/1995 | Zlotnik et al. |
| 5,445,802 A | 8/1995 | Wendelken |
| 5,465,198 A | 11/1995 | Kellogg |
| 5,480,591 A | 1/1996 | Lagneaux et al. |
| 5,481,442 A | 1/1996 | Dickie et al. |
| 5,484,086 A | 1/1996 | Pu |
| 5,498,397 A | 3/1996 | Horng |
| 5,521,357 A | 5/1996 | Lock et al. |
| 5,522,008 A | 5/1996 | Bernard |
| 5,547,616 A | 8/1996 | Dancs et al. |
| 5,556,192 A | 9/1996 | Wang |
| 5,567,361 A | 10/1996 | Harper |
| 5,574,821 A | 11/1996 | Babasade |
| 5,575,992 A | 11/1996 | Kunze |
| 5,577,156 A | 11/1996 | Costello |
| 5,591,395 A | 1/1997 | Schroeder et al. |
| 5,624,230 A | 4/1997 | Taylor et al. |
| 5,634,806 A | 6/1997 | Hahn |
| 5,647,052 A | 7/1997 | Patel et al. |
| 5,647,053 A | 7/1997 | Schroeder et al. |
| 5,651,942 A | 7/1997 | Christinsen |
| 5,662,835 A | 9/1997 | Collingwood |
| 5,664,958 A | 9/1997 | Chadwick et al. |
| 5,700,430 A | 12/1997 | Bonnema et al. |
| 5,735,460 A | 4/1998 | Eisenbraun |
| 5,749,520 A | 5/1998 | Martin et al. |
| 5,750,498 A | 5/1998 | Soeda et al. |
| 5,765,751 A | 6/1998 | Joshi |
| 5,788,155 A | 8/1998 | Martin et al. |
| 5,788,931 A | 8/1998 | Munoz Quintana |
| 5,796,914 A | 8/1998 | Gatzemeyer et al. |
| 5,805,768 A | 9/1998 | Schwartz et al. |
| 5,810,265 A | 9/1998 | Cornelius et al. |
| 5,813,873 A | 9/1998 | McBain et al. |
| 5,832,648 A | 11/1998 | Malone |
| 5,873,529 A | 2/1999 | Johnson |
| 5,875,968 A | 3/1999 | Miller et al. |
| 5,884,808 A | 3/1999 | Muderlak et al. |
| 5,899,381 A | 5/1999 | Gordon et al. |
| 5,903,710 A | 5/1999 | Wefler et al. |
| 5,926,614 A | 7/1999 | Steinel |
| 5,928,605 A | 7/1999 | Bonnema et al. |

| | | | | | | |
|---|---|---|---|---|---|---|
| 5,932,204 A | 8/1999 | Joshi | | 6,368,564 B1 | 4/2002 | Smith |
| 5,937,140 A | 8/1999 | Leonard et al. | | 6,371,815 B1 | 4/2002 | Wetzel et al. |
| 5,940,577 A | 8/1999 | Steinel | | 6,374,044 B1 | 4/2002 | Freidel |
| 5,944,223 A | 8/1999 | Klima et al. | | 6,374,045 B2 | 4/2002 | Basaganas Millan |
| 5,945,094 A | 8/1999 | Martin et al. | | 6,381,408 B1 | 4/2002 | Jaworski et al. |
| 5,955,701 A | 9/1999 | Schockner et al. | | 6,603,924 B2 * | 8/2003 | Brown et al. ............... 392/390 |
| 5,957,701 A | 9/1999 | McMillin | | 6,661,967 B2 * | 12/2003 | Levine et al. ............... 392/395 |
| 5,970,643 A | 10/1999 | Gawel, Jr. | | 6,714,725 B2 | 3/2004 | Grone et al. |
| 5,976,503 A | 11/1999 | Martin et al. | | 2001/0031225 A1 | 10/2001 | Mandish |
| 5,998,735 A | 12/1999 | Patterson, Jr. | | 2001/0053283 A1 | 12/2001 | Levine et al. |
| 6,021,254 A | 2/2000 | Hunter | | 2002/0144992 A1 | 10/2002 | Vieira |
| 6,031,967 A | 2/2000 | Flashinski et al. | | 2003/0138241 A1 | 7/2003 | Ambrosi et al. |
| 6,032,930 A | 3/2000 | Calino | | | | |
| 6,036,536 A | 3/2000 | Chiu | | | | |
| 6,044,202 A | 3/2000 | Junkel | | | | |

FOREIGN PATENT DOCUMENTS

| | | |
|---|---|---|
| EP | 0 669 137 | 8/1995 |
| EP | 0 911 041 | 4/1999 |
| GB | 402507 | 12/1933 |
| GB | 2 356 815 | 6/2001 |
| WO | WO 00 76292 | 12/2000 |
| WO | WO 01 10739 | 2/2001 |
| WO | WO 01/68154 | 9/2001 |
| WO | WO 01/93919 | 12/2001 |

| | | |
|---|---|---|
| 6,045,374 A | 4/2000 | Candeloro |
| 6,050,551 A | 4/2000 | Anderson |
| 6,051,788 A | 4/2000 | Nichols |
| 6,078,728 A | 6/2000 | O'Rourke et al. |
| 6,085,026 A | 7/2000 | Hammons et al. |
| 6,097,881 A | 8/2000 | DeWitt et al. |
| 6,099,137 A | 8/2000 | McCormack et al. |
| 6,101,315 A | 8/2000 | Steinel, Jr. |
| 6,104,866 A | 8/2000 | DeWitt et al. |
| 6,104,867 A | 8/2000 | Stathakis et al. |
| D430,659 S | 9/2000 | Zaraboza et al. |
| 6,123,935 A | 9/2000 | Wefler et al. |
| 6,141,496 A | 10/2000 | Sundberg et al. |
| 6,148,143 A | 11/2000 | Steinel, Jr. |
| 6,156,088 A | 12/2000 | Cardarelli |
| 6,197,262 B1 | 3/2001 | Del Ben |
| 6,197,263 B1 | 3/2001 | Blount |
| 6,227,118 B1 | 5/2001 | Nance |
| 6,236,807 B1 | 5/2001 | Ruffolo et al. |
| 6,249,645 B1 | 6/2001 | Smith |
| 6,254,065 B1 | 7/2001 | Ehrensperger et al. |
| 6,264,548 B1 | 7/2001 | Payne, Jr. et al. |
| 6,269,979 B1 | 8/2001 | Dumont |
| 6,270,720 B1 | 8/2001 | Mandish |
| 6,275,651 B1 | 8/2001 | Voit |
| 6,278,840 B1 | 8/2001 | Basaganas Millan |
| 6,285,830 B1 | 9/2001 | Basaganas Millan |
| 6,289,176 B1 * | 9/2001 | Martter et al. ............... 392/392 |
| 6,302,559 B1 | 10/2001 | Warren |
| 6,315,959 B2 | 11/2001 | Mandish |
| 6,328,791 B1 | 12/2001 | Pillion et al. |
| 6,342,676 B1 | 1/2002 | Ha |
| 6,349,168 B1 | 2/2002 | Jaworski |
| 6,352,210 B1 | 3/2002 | Requejo |
| 6,354,513 B1 | 3/2002 | Basaganas Millan |
| 6,361,752 B1 | 3/2002 | Demarest et al. |
| 6,364,673 B1 | 4/2002 | Lee |

OTHER PUBLICATIONS

PCT International Search Report issued Apr. 21, 2004 for International Application No. PCT/US03/26754, International Filing Date Aug. 28, 2003, 4 pages.

PCT International Search Report issued Nov. 12, 2003 for International Application No. PCT/US03/25245, International Filing Date Aug. 13, 2003, 4 pages.

PCT International Search Report issued Oct. 7, 2003 for International Application No. PCT/US03/04082, International Filing Date Feb. 12, 2003, 8 pages.

PCT International Search Report issued Dec. 16, 2003 for International Application No. PCT/US03/25244, International Filing Date Aug. 13, 2003, 3 pages.

PCT International Search Report issued Dec. 16, 2003 for International Application No. PCT/US03/25246, International Filing Date Aug. 13, 2003, 3 pages.

PCT International Search Report issued Dec. 19, 2003 for International Application No. PCT/US03/25243, International Filing Date Aug. 13, 2003, 4 pages.

Brochure– "Decora Devices," by Leviton, date unknown, Section A, pps. A1–A36.

PCT Written Opinion issued Jul. 19, 2004 for International Application No. PCT/US03/25245, International Filing Date Aug. 13, 2003, 5 pages.

* cited by examiner

METHODS AND APPARATUS FOR A CONTROLLABLE VAPOR-DISPENSING DEVICE

CROSS-REFERENCE TO RELATED APPLICATIONS

This application is a continuation-in-part of U.S. patent application Ser. No. 10/222,500 entitled "Methods And Apparatus for a Controllable Vapor-Dispensing Device" filed Aug. 16, 2002 which is incorporated herein by reference.

TECHNICAL FIELD

This invention relates, generally, to vapor dispensing devices and, in particular, to a vapor-dispensing device that exhibits a high degree of controllability over a range of sensory fragrance intensities.

BACKGROUND INFORMATION

Vapor-dispensing devices such as air-fresheners and the like typically include a reservoir and a transport system from which a fragrance or other volatizable material can be evaporated into the surrounding environment. As an individual's subjective response to an airborne fragrance will vary according to, inter alia, the nature of the scent, the olfactory sensitivity of the individual, and the extent to which other unwanted odors exist in the environment, it is not unusual for such vapor-dispensing devices to include some form of apparent control over the intensity of fragrance or other vapor released into the environment. These control-systems typically take the form of adjustable venting configurations and or components which selectively adjust the proximity of a heating element to the wick and/or reservoir of volatizable material.

Such methods of providing a controlled amount of vapor may be unsatisfactory in a number of respects. For example, while known vapor-dispensing devices allow the user to move a slider, knob, or other such control to modulate fragrance output, the resulting effect on actual evaporation rate may be negligible, resulting in a device which effectively delivers vapor at a single evaporation rate.

Even in cases where the evaporation rate of a prior art vapor-dispensing device offers a range of evaporation rates, the actual corresponding range of sensory fragrance intensity values (i.e., the actual subjective response to particular vapor density and/or evaporation rates) may often be indiscernible.

Furthermore, such prior art devices typically function at only the extremes of their operating range; i.e.—while the device might include a slider, knob, or other such component which can be moved over a continuous range (or between a number of discrete settings), the device itself will generally not operate at intermediary values falling within the continuous range.

Thus, there exists a need for a vapor-dispensing device which is controllable and which operates between a meaningful range of sensory fragrance intensities.

SUMMARY OF THE INVENTION

While the way in which the present invention addresses the disadvantages of the prior art will be discussed in greater detail below, in general, the present invention provides a vapor-dispensing device exhibiting a range of evaporation rates corresponding to a discernable range of sensory fragrance intensity levels. In accordance with a further aspect of the present invention, the vapor-delivery device includes one or more control structure (e.g., a heat control, a vent control, and/or the like) configured to allow a user to specify the evaporation rate of the vapor-dispensing device over a continuous or discretized range of values. In accordance with another aspect of the present invention, the two extremes of operation correspond to a range of sensory fragrance intensity values that span (or include) at least three minimum perceivable intensity zones.

BRIEF DESCRIPTION OF THE DRAWINGS

The subject invention will hereinafter be described in conjunction with the appended drawing figures, wherein like numerals denote like elements, and.

DETAILED DESCRIPTION

Systems and methods in accordance with the present invention generally provide for a vapor-dispensing device exhibiting a range of evaporation rates corresponding to a discernable range of sensory fragrance intensity levels. In accordance with a further aspect of the present invention, the vapor-delivery device includes one or more control structure (e.g., a heat control, a vent control, and/or the like) configured to allow a user to specify the evaporation rate of the vapor-dispensing device over a continuous or discretized range of values.

Figure 1:
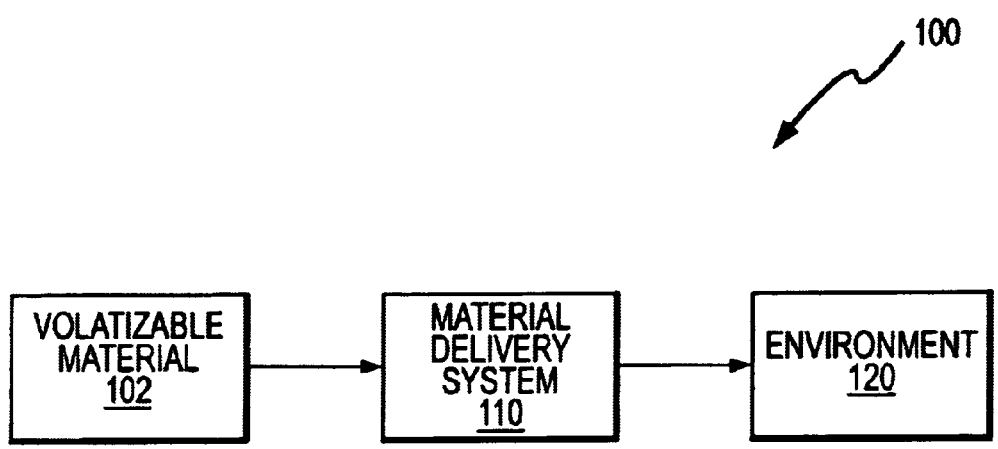
FIG. 1 is a schematic overview of a system providing a context in which the present invention may be practiced.

Referring to FIG. 1, a vapor-dispensing device in accordance with the present invention generally comprises a material delivery system (or simply "delivery system") 110 connected to or indirectly coupled to a volatizable material 102 and an environment 120. Material delivery system 110 comprises any suitable component or combination of components configured to communicate with both volatizable material 102 and environment 120 as described further below.

Volatizable material 120 comprises one or more suitable liquids, waxes, colloids, gels, solids, or other form of matter which may be caused to evaporate, sublimate, or otherwise transformed to a vapor. In one embodiment, volatizable material 120 comprises a natural or synthetic oil bearing a fragrance—i.e., an oil infused with one or more materials (floral, citrus, exotic spices, etc.). Volatizable material 120 may be self-contained, or may be all or partially held within a reservoir, bottle, or other such container.

Environment 120 corresponds to any defined space, whether open or enclosed by one or more surfaces, walls, ceilings, floors, or other solid or fictitious boundaries, which receives the evaporated material. For example, environment 120 may correspond to a residential room (bedroom, bathroom, kitchen, etc.), commercial space (factory floor, office cubicles, etc.), automotive enclosure (car, truck, recreational-vehicle), airline compartment, or any other space in which it is desirable to deliver a vapor.

Figure 6:
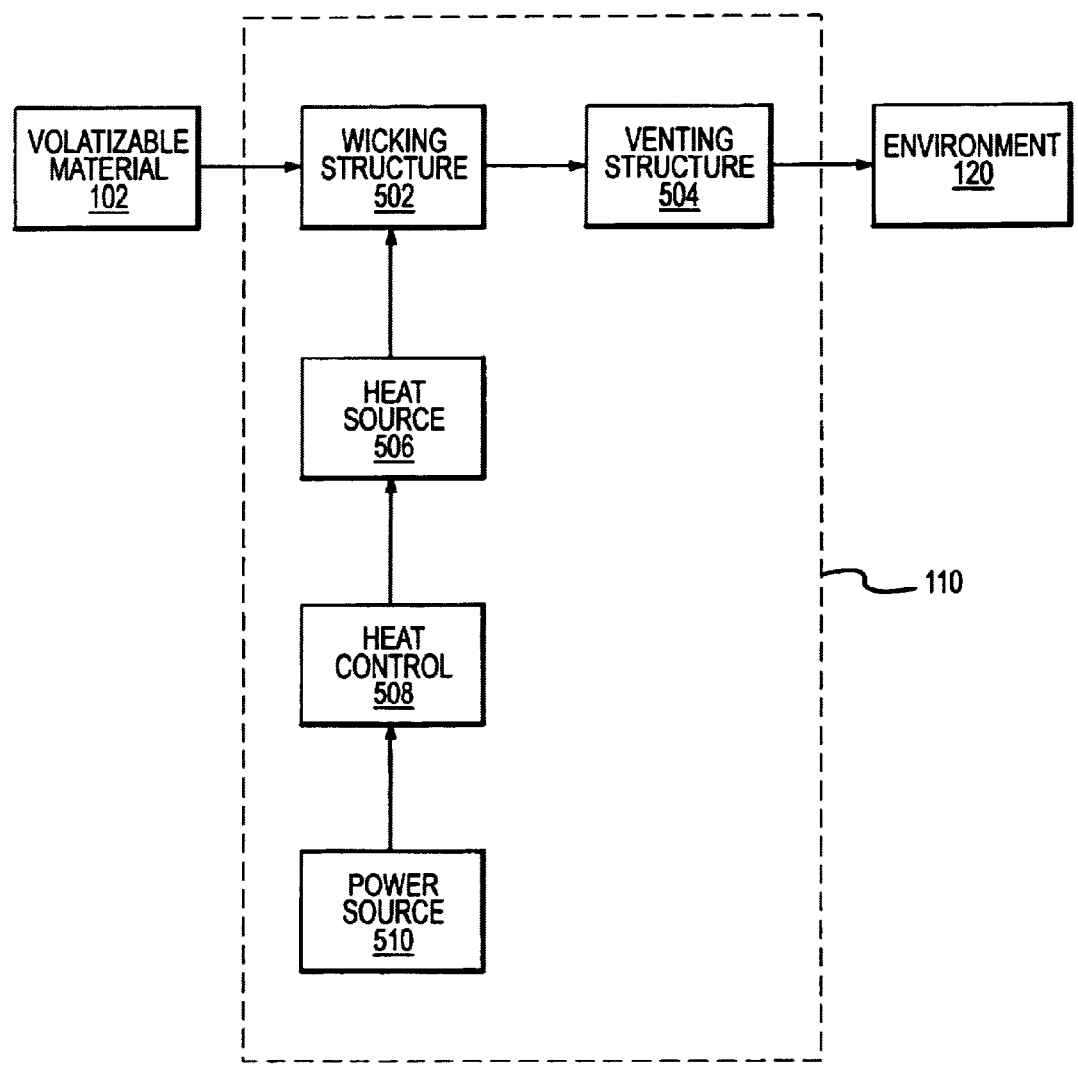
FIG. 6 is a schematic block diagram of a vapor dispensing device in accordance with the present invention.

FIG. 6 presents a block-diagram of a system in accordance with various aspects of the present invention wherein an exemplary material delivery system 110 has been illustrated in more detail. As shown, material delivery system 110 may suitably comprise a wicking structure 502 coupled to volatizable material 102 and optional venting structure 504. Wicking structure 502 is thermally coupled to heat source 506 (e.g, a resistive element, heating coil, or the like), the temperature of which is suitably controlled via heat control 508 (e.g., a variable resistor in series with heat source 506). Heat control 506 (and/or heat source 506) are electrically coupled to a power source 510, wherein power source 510 comprises any source capable of providing the necessary current and voltage to heat source 506. Suitable power sources include, for example, standard household AC outlets, one or more batteries, solar power, etc.

Figure 7:
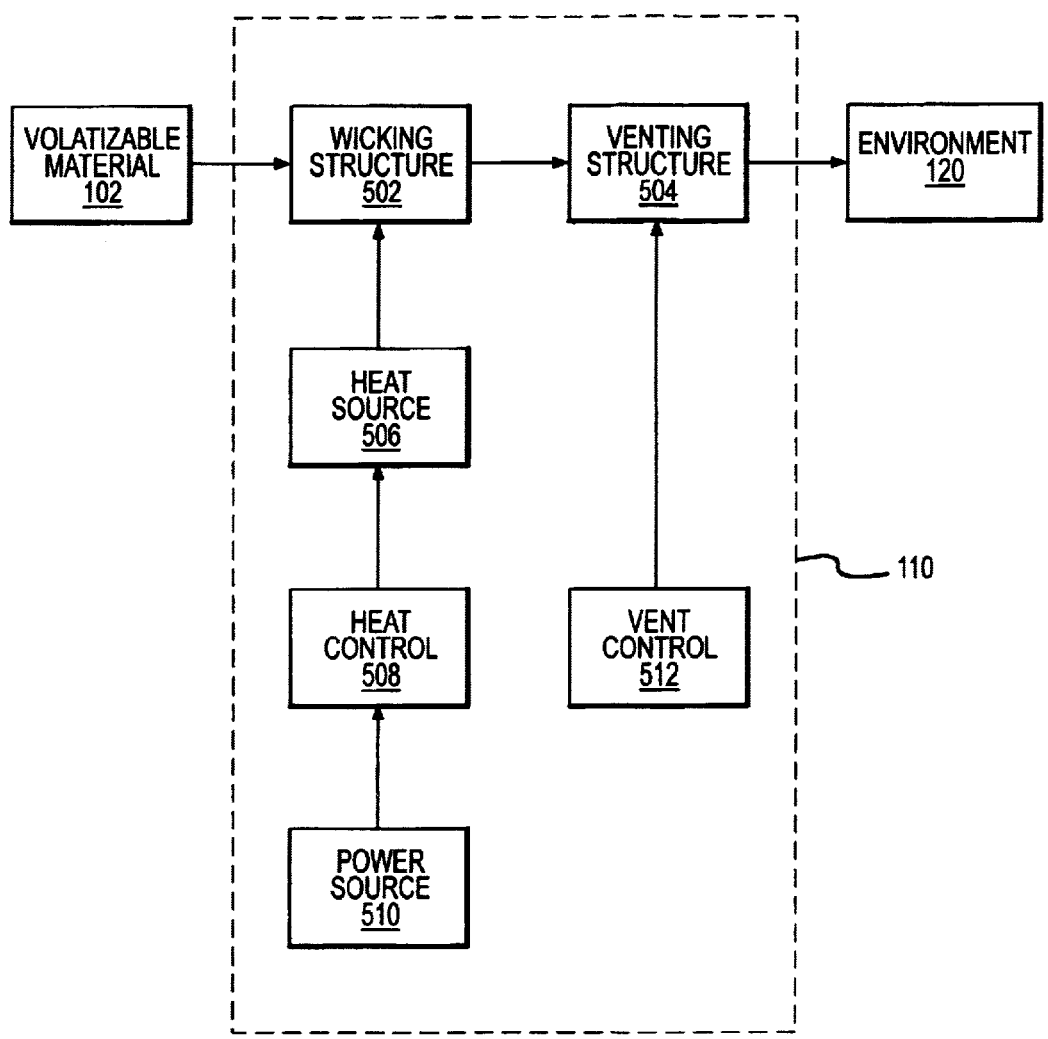
FIG. 7 is a schematic block diagram of a vapor dispensing device in accordance with a further embodiment of the present invention.

In accordance with an exemplary embodiment, material delivery system 110 and volatizable material 102 form a self-contained unit that includes one or more plugs configured to attach to an electrical receptacle, for example, a duplex AC power outlet. The heat source 506 then receives power indirectly from the AC outlet—i.e., through appropriate static and/or variable resistors. One or more fuseable links may be included to the circuit to prevent potential damage resulting from over-current conditions. In an alternate embodiment, shown in FIG. 7, a vent control 512 is coupled to venting structure 504.

Figure 8:
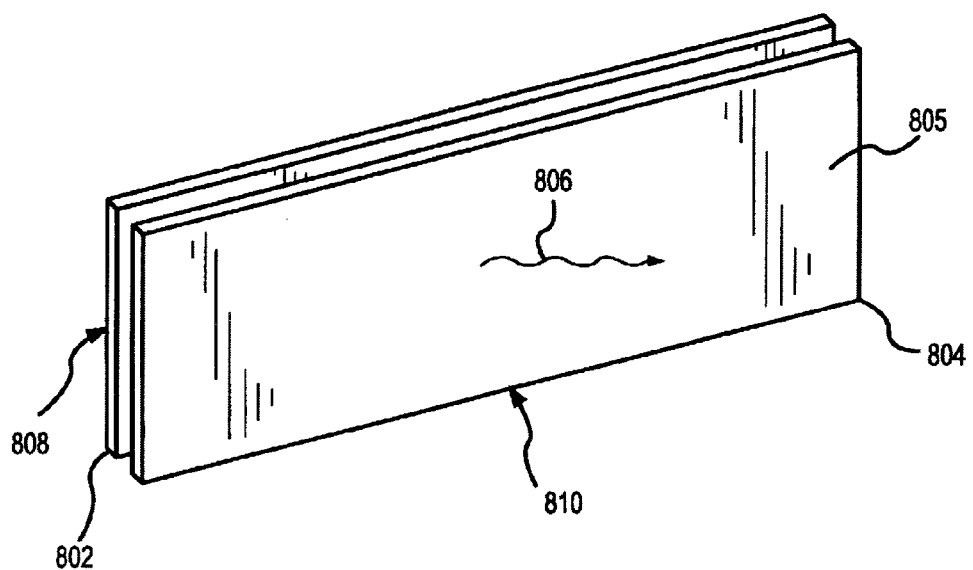
FIG. 8 depicts a heat source and eminator pad in accordance with one embodiment of the present invention.

Further in accordance with an exemplary embodiment, wicking structure 502 includes an eminator pad (or simply "pad") which may or may not comprise the same material used for other components of wicking structure 502, which is thermally coupled to a thin film resistive element capable of heating the eminator pad to a range of surface temperatures. More particularly, referring now to FIG. 8, one embodiment of the present invention comprises a pad 804 is coupled to volatizable material 810 and provides a surface 805 which interfaces with the environment, thus facilitating mass transfer 806 (e.g.) of the volatizable material. Heat source 802 (which receives a modulated current 808) is thermally coupled to pad 804. The thermal coupling between pad 804 and heat source 802 may be in the nature of conduction, convection, radiation, or a combination thereof In one embodiment, for example, heat transfer between pad 804 and heat source 802 is accomplished primarily through conduction. That is, pad 804 may directly contact heat source 802 (through, for example, a compression fit) or may be thermally coupled to heat source 802 through one or more intermediary layers of plastic or other material.

Figure 9C:
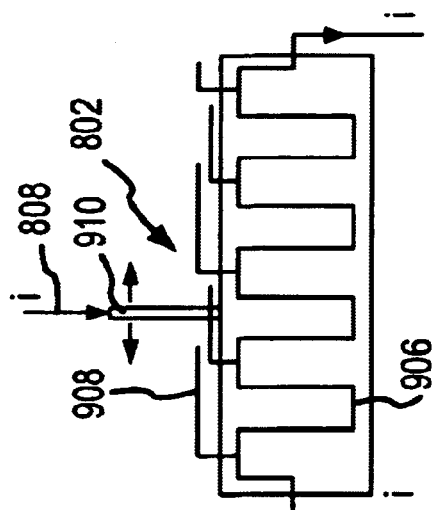
FIGS. 9A–9C show various heat source configurations in accordance with the present invention.

Heat source 802 may comprise any suitable material and structure capable of heating pad 804 within the desired range. For example, referring now to FIG. 9A, heat source 802 may comprise a contiguous region 902 of thin film material (e.g., carbon, graphite, or the like) having a specified film resistance and which generates heat in response to current flow 808.

Figure 9B:
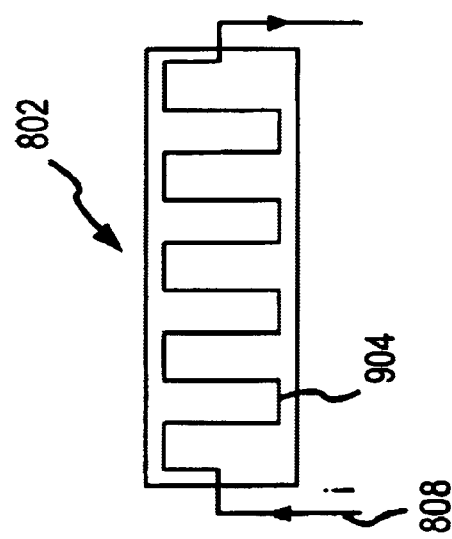
Figure 9A:
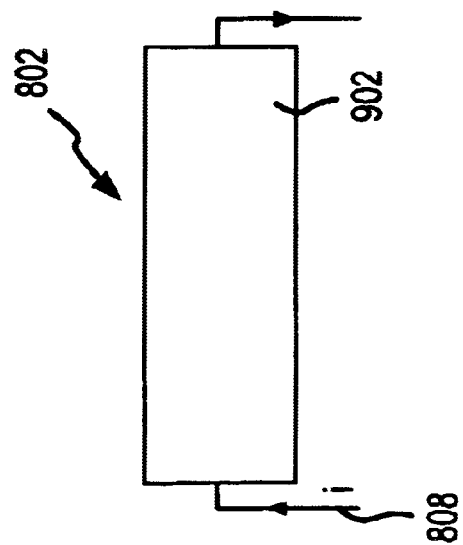

In an alternate embodiment, shown in FIG. 9B, heat source 802 comprises a generally serpentine pattern of resistive material 904. In yet another embodiment (FIG. 9C), a plurality of taps 908 extend from 906 at various points to allow a moveable controller terminal 910 (e.g., a slider or other rheostat control) to contact the various taps 908 as it traverses the length of heat source 802. This allows the heat source 802 to generate discrete temperature values.

Pad 804 may be configured as any convenient continuous shape (e.g., rectangular, elliptical, square, triangular, or any other arbitrary rectilinear or curvilinear shape) or may comprise multiple segmented regions of the same or varying shapes. In one embodiment, pad 804 has a generally rectangular shape with a total surface area of approximately 5.0 to 15.0 square centimeters, preferably about 10 square centimeters.

Figure 10:
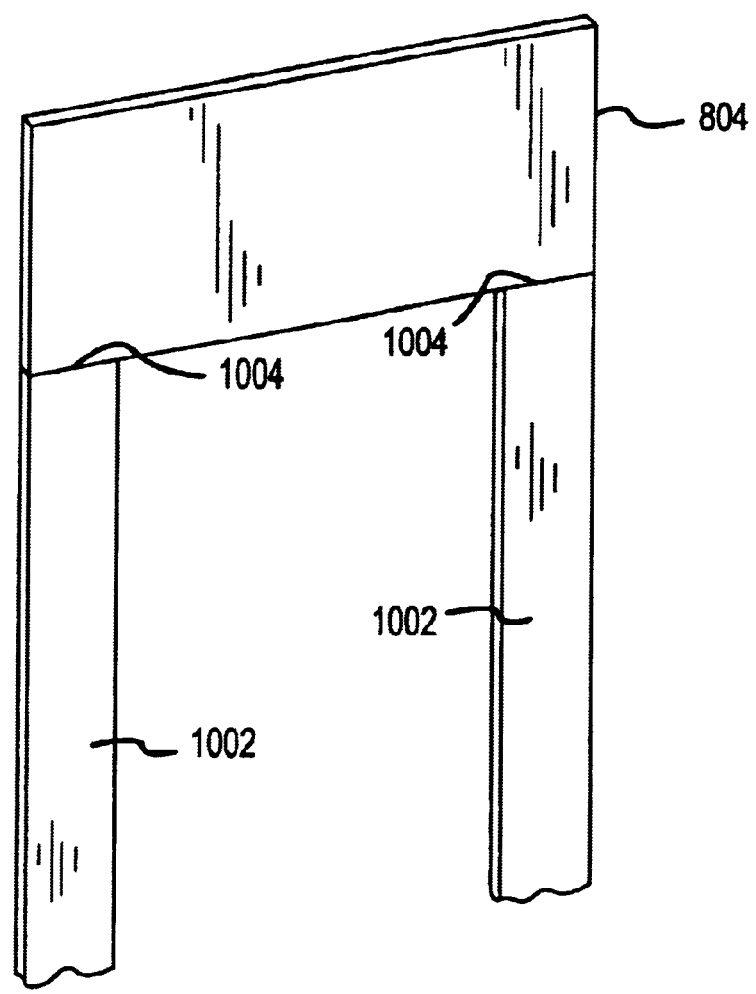
FIG. 10 shows a wick/eminator configuration in accordance with the present invention.

Pad 804 may receive the supply 810 of volatizable material via one or more wicks communicating with one or more reservoirs of volatizable material. Referring to FIG. 10, for example, pad 804 may communicate with a pair of wicks 1002 at corresponding contact points 1004 remotely located along pad 804. Any number of wicks may be provided, and the nature of contact points 1004 corresponding to each wick may be selected to optimize material delivery rate or any other attribute of the system. For example, wicks 1002 may be compressively attached to pad 804 at contact points 1004 such that a contact area is formed. Alternatively, wicks 1002 may be an integral extension of pad 804.

While various embodiments of vapor-dispensing devices have been described herein, it should be appreciated that any device capable of being configured to exhibit a high degree of controllability over a range of sensory fragrance intensities, as will be described in greater detail below, may be utilized in accordance with the present invention.

Having thus given an overview of a vapor-dispensing device in accordance with the present invention, the operational details of such a system will now be described.

Figure 2:
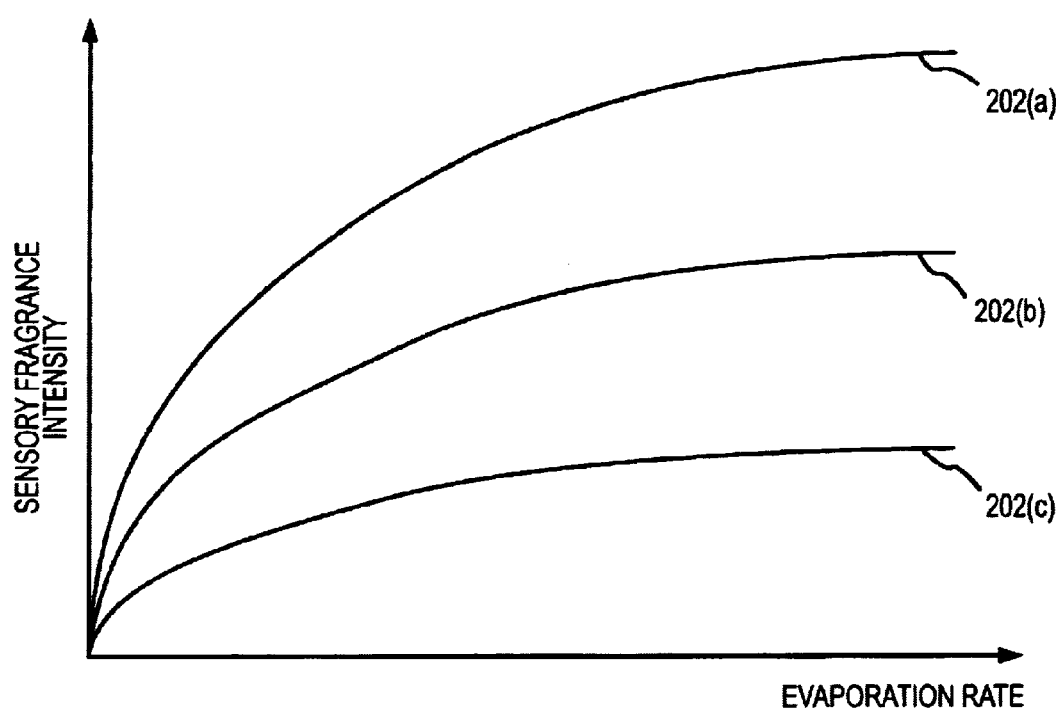
FIG. 2 shows the qualitative relationship between sensory fragrance intensity and evaporation rate.

It is known that human olfaction does not respond linearly to an increase in fragrance density in an environment. That is, as the fragrance density in a room increases, the marginal increase in fragrance density required to cause an individual to notice that difference also increases. This effect is illustrated qualitatively in FIG. 2. As shown, sensory fragrance intensity (i.e., the subjective perception of fragrance intensity by an individual) is related to evaporation rate (assuming a room of constant volume, with an individual sampling the environment at a given time) by a series of non-linear curves 202 corresponding to individual volatizable material compositions. Thus, a particular composition 202(*a*) (e.g., pine scent) may result in a higher sensory fragrance intensity than another composition 202(*b*) (e.g., vanilla scent) for any given evaporation rate.

Figure 3:
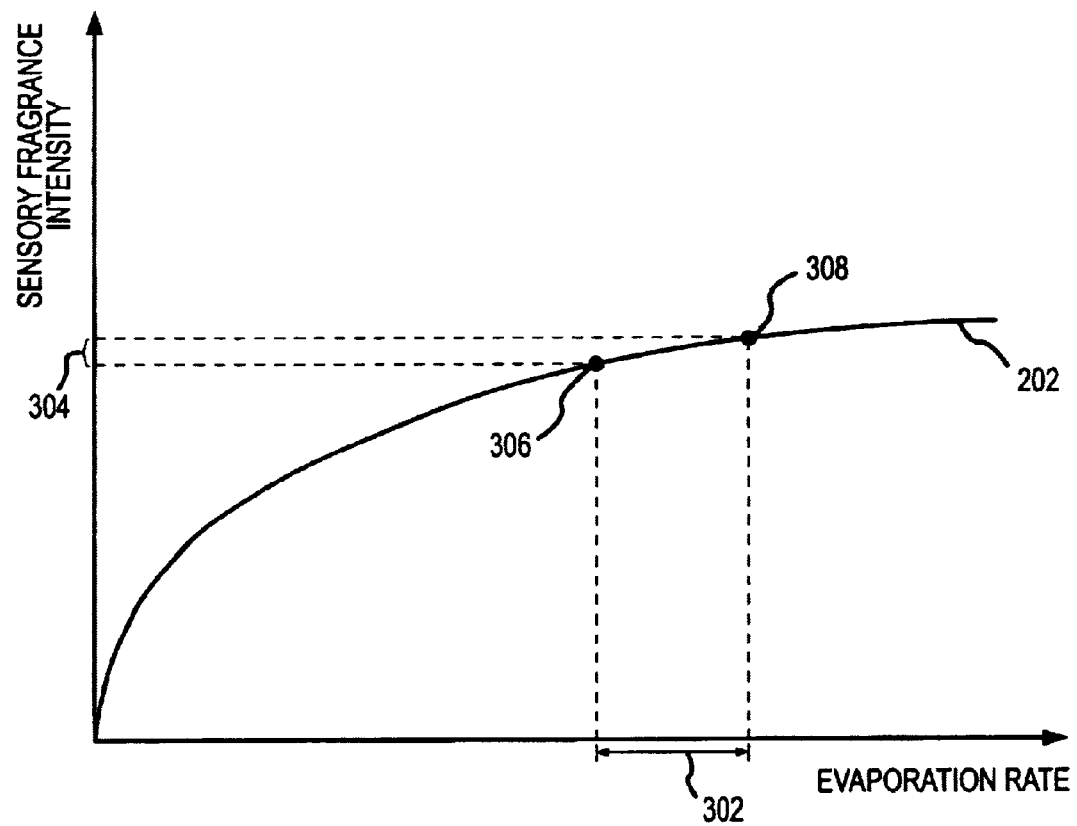
FIG. 3 depicts the sensory fragrance intensity range of a typical prior art vapor dispensing device.

As mentioned briefly in the Background section, prior art vapor dispensing devices do not allow the user to have any real control over the sensory fragrance intensity of the unit. Referring now to FIG. 3, a typical prior art vapor dispensing device may include some form of illusory control mechanism (i.e., an adjustable vent) which allows the unit to operate at two points 306 and 308 along the sensory fragrance intensity curve 202. While this pair of points may correspond to a relatively meaningful evaporation rate range 302, the actual change in sensory fragrance intensity (304) is quite small—i.e., a difference that is generally indiscernible by an individual.

Figure 4:
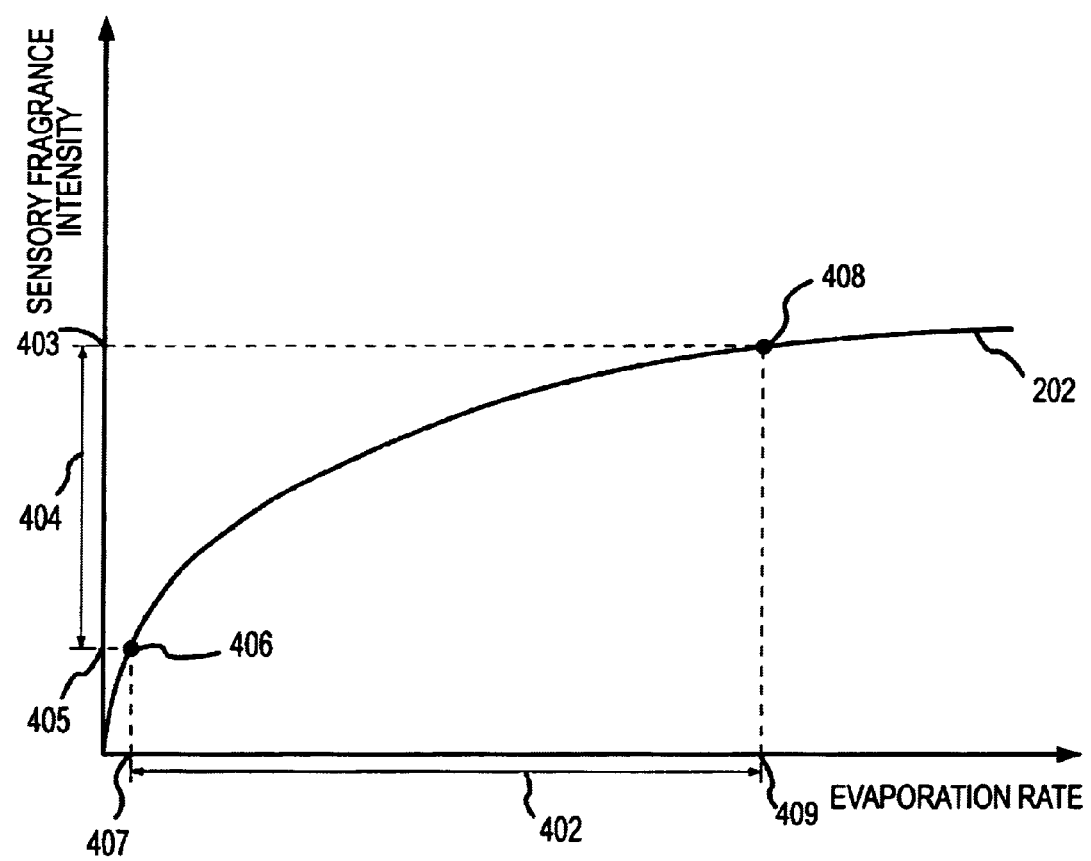
FIG. 4 depicts a sensory fragrance intensity range of a vapor dispensing device in accordance with the present invention.

Referring now to FIG. 4, a vapor dispensing device in accordance with one aspect of the present invention provides an improved range of sensory fragrance intensity values by operating along a more advantageous region of the sensory fragrance intensity curve. More particularly, for a given volatizable material composition, a vapor dispensing device operates over a range 402 extending from a minimum evaporation rate 407 to a maximum evaporation rate 409. Minimum evaporation rate 407 generally corresponds (under a specified test conditions) to a minimum sensory fragrance intensity 405, and maximum evaporation rate 409 generally corresponds to a maximum sensory fragrance intensity 403, thus exhibiting a sensory fragrance intensity range 404. Thus, the vapor dispensing device operates at two or more points (408, 406) along curve 202.

In accordance with one embodiment of the present invention, the minimum evaporation rate 407 is between about 2.0 and 20 mg/hr or, more particularly, between about 5.0 and about 15.0 mg/hr, preferably about 10.0 mg/hr. The maximum evaporation rate 409 is between about 30.0 and 100.0 mg/hr or, more particularly, between about 30.0 and about 50.0 mg/hr, preferably about 40.0 mg/hr. Accordingly, the range 402 of evaporation rates is suitably between about 2.0 and about 100.0 mg/hr, preferably between about 5.0 and 50 mg/hr.

Furthermore, the device may have a "medium setting" corresponding to an evaporation rate of between about 10.0 and 40.0 mg/hr, preferably between about 15.0 and 30 mg/hr, most preferably about 20 mg/hr.

In addition, the device may have an evaporation efficiency characterized the maximum evaporation rate divided by the maximum power input. For example, a maximum power input of about 1.8 watts and a maximum rate of about 100 mg/hr yields an evaporation efficiency of about 55.0 mg/W·hr. In accordance with one aspect of the present invention, the evaporation efficiency is greater than or equal to about 40–60 mg/W·hr, preferably about 55 mg/W·hr.

In accordance with another aspect of the present invention, the controller is configured to modulate the power input between a minimum power input and a maximum power input, wherein the maximum power input corresponds to a maximum evaporation rate and a maximum surface temperature. The device can then be characterized by a thermal evaporation efficiency defined as the maximum evaporation rate divided by the maximum surface temperature. In accordance with one embodiment of the present invention, the thermal evaporation efficiency is greater than or equal to approximately 1.0 to 2.0 mg/hr·° C., preferably about 1.5 mg/hr·° C. (e.g., at a 100 mg/hr evaporation rate and 66° C. maximum surface temperature).

As mentioned above, it is possible for two different evaporation rates to result in the same perceived fragrance intensity. Thus, in accordance with a further aspect of the present invention, a vapor dispensing device has a range of evaporation rates which traverse at least three minimum perceivable intensity zones. This aspect is illustrated in FIG. 5.

Figure 5:
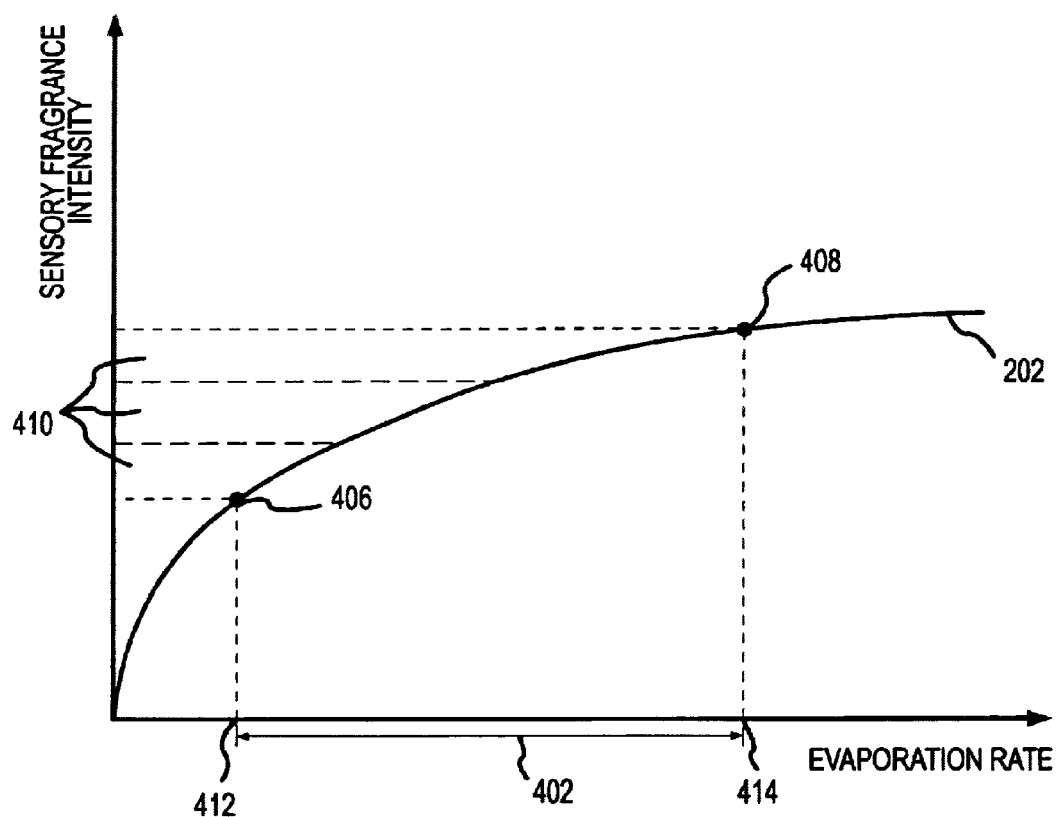
FIG. 5 depicts a sensory fragrance intensity range in accordance with another aspect of the present invention.

As shown in FIG. 5, the vapor dispensing device exhibits a range of evaporation rates 402 between minimum and maximum evaporation rates 412 and 414 respectively. The two extremes of operation along curve 202 (points 406 and 408) correspond to a range of sensory fragrance intensity values that span (or include) at least three minimum perceivable intensity zones (or simply "zones") 410. The nature of zones 410 (including, for example, whether the zones significantly overlap) will vary depending upon, among other things, the type of fragrance employed (or, more generally, the volatizable material), as one fragrance may have a smaller zone (i.e., is more likely to be perceived by an individual) than a second fragrance.

In accordance with another embodiment of the present invention, the range of evaporation rates span at least two minimum perceivable intensity zones for the volatizable material, wherein the minimum perceivable intensity zones are substantially non-overlapping.

The nature of zones 410 may be derived via simulation or, preferably, actual empirical testing of target fragrances. More particularly, controlled tests may be performed to determine what level of fragrance delivery is necessary to caused a perceived change in fragrance intensity.

Any convenient test procedure and statistical testing technique may be used. In general, however, a test device (i.e., a vapor dispensing device of interest) is placed in a room whose environment has been substantially cleared of unwanted odors (e.g., fragrances from prior tests). In this regard, the size and shape of the test room may be selected in accordance with a variety of design factors. In one embodiment, for example, the test room comprises a generally rectangular space having a volume of about 700–1000 cubic feet, e.g., about 810 cubic feet.

The temperature and relative humidity of the test room are preferably controlled at suitable levels, for example, levels which are comparable to the environment in which the vapor dispensing device is likely to be employed. In accordance with an exemplary test procedure, the test room is maintained at between about 68–76° F., preferably about 72° F., and the relative humidity is maintained at between about 30% and 50%, preferably about 40%.

The test device is preferably blocked from view (without blocking functionality) to prevent any skewing of test data that might result from the subject's observation of the test unit's physical appearance. The evaporation rate characteristics of the test unit are suitably determined prior to, during, or after testing, e.g., by measuring the weight loss of the device or comparable devices over time.

The test device is allowed to operate for a specific time period. A set of pre-selected test subjects are then directed to (or, in the case of double-blind testing, escorted into) the test room where they are instructed to rate the subjective intensity of the perceived fragrance on a suitable scale. The fragrance intensity scale may be numeric and/or alphabetical, and may have any desired level of resolution. In an exemplary embodiment, the test subjects are asked to rate the test unit on a numeric scale from 1 to 9, inclusive, where 1 corresponds to "no fragrance detected," and 9 corresponds to "extremely strong."

This test is performed for multiple test devices and/or identical test devices with multiple control settings. The test subjects are preferably provided a suitable rest time, for example 30 seconds, between trials. Any number of test subjects may be used, and the test may be repeated any number of times depending upon the level of confidence required. In an exemplary testing scheme, for example, about 10 to 30 subjects are used (preferably about 20), and the testing involves two trials, with the order of test subjects preferably randomized in both trials.

After the test results are compiled, suitable statistical analysis is performed to determine whether the average differences between the evaporation rates or test units are statistically significant to a specified confidence level (e.g., a 95% confidence level). This analysis may take the form of standard A-B "F-tests", analysis of variance (ANOVA), conventional regression methods, or any other convenient technique. In this way, statistical groups (i.e., "a", "b", "c", and "d" groupings) for the various devices and settings may be derived, and the minimum perceivable intensity zones may be characterized for a given fragrance.

Information regarding standardized odor intensity testing may be found, for example, in ASTM Standard E 544-99, Standard Practices for Referencing Suprathreshold Odor Intensity. Additional information regarding planned experiments, regression testing, and the like may be found, for example, in DOUGLAS MONTGOMERY AND ELIZABETH PECK, INTRODUCTION TO LINEAR REGRESSION ANALYSIS, 2d ed (1992).

Referring again to FIG. 6, the function of the various components of delivery system 110 will be described. In general, material delivery system 110 assists in transport and evaporation of volatizable material 102 through the use of, for example, a wicking structure 502. The temperature of heat source 506 is suitably controlled via heat control 508 (e.g., a human-accessible variable resistor in series with heat source 506), which draws electrical current from power source 510 and converts the electrical current to thermal energy which is at least partially communicated with wicking structure 502. In accordance with various embodiments of the present invention, material delivery system 110 includes one or more components (e.g., wicks, capillary tubes, and the like) which enable the transport of volatizable material 102 from one location to another (e.g., from a reservoir to a evaporation pad or eminator), and/or one or more components (eminator pads, secondary wicks, and the like) which provide a surface or surfaces from which the transported material undergoes mass transfer or evaporation to environment 120 and which offers real control. As described in further detail below, material delivery system 110 may also include one or more controls configured to modulate the rate at which volatizable material 102 is delivered to environment 120.

Exemplary material delivery system 110 has two primary functions: material transport and material vaporization. Accordingly, wicking structure 502 includes one or more components (e.g., wicks, capillary tubes, and the like) directed at transporting volatizable material 102 from one location to another (e.g., from a reservoir to a evaporation pad or eminator), and one or more components (eminator pads, secondary wicks, and the like) which provide a surface or surfaces from which the transported material undergoes mass transfer to environment 120.

The resulting vapor enters environment 120, the rate of which is controlled through a suitable venting structure 504 and/or heat source 506. As mentioned above, one embodiment of the present invention comprises a pad 804 which receives a supply of volatizable material 810 and provides a surface 805 which interfaces with the environment, thus facilitating mass transfer 806 (e.g.) of the volatizable material. Heat source 802 (which receives a modulated current 808) is thermally coupled to pad 804, and may comprise any suitable material and structure capable of heating pad 804 within the desired range. In an alternate embodiment, shown in FIG. 9B, heat source 802 comprises a generally serpentine pattern of resistive material 904 which generates heat in response to current 808.

The resistivity and geometry of heat source 802, as well as the range of currents 808 which are applied to heat source 802, may be selected to afford any desired range of temperature values. In an exemplary embodiment, heat source 802 has the following thermal characteristics: a temperature of approximately 140° F. to 160° F. at a high setting (of heat control 508); a temperature of approximately 100° F. to 130° F. at a medium setting; and a temperature of approximately 110 to 120° F. at a low setting.

Further in accordance with the exemplary embodiment, the total resistance of heat source 802 is approximately 1000 to 1250 Ohms, preferably about 1250 Ohms, and the supply current 808 ranges from about 15 mA at the low setting to about 60 mA at the high setting. Pad 804 may comprises any suitable material selected to provide sufficient transport and evaporation properties.

It will be appreciated that while various embodiments of the present invention, including the delivery system, have been described as having a wick, heat source, reservoir, or the like, the present invention is not so limited. Indeed, the present invention contemplates that the delivery system comprises any conceivable structure configured to facilitate evaporation of volatizable material into an environment.

The delivery system may comprise, for example, a structure which surrounds, encapsulates, or otherwise provides a boundary (e.g., an adjustable boundary) between the volatizable material and the environment. In the event that volatizable material comprises a substantially solid material such as wax, the material delivery system may comprises any suitable structure, but might also simply comprise an extrinsic property of the volatizable material itself, e.g., a particular shape, orientation, texture, or other predetermined characteristic. For example, the volatizable material may comprise a substantially rigid block of scented wax whose shape and orientation are selected to interface with the environment in a desired manner.

In the event that the volatizable material comprises a semi-solid form, such as gel, the material delivery system might take the form of a reservoir, dish, chamber, or other structure which entirely or partially surrounds the gel. The surrounding structure might be substantially impermeable, partially impermeable, or permeable. For example, the surrounding structure might include a venting or perforation geometry which assists in evaporation while at the same time providing structural support for the gel.

In the event that the volatizable material comprises a liquid, the material delivery system might be as simple as an open reservoir, bottle, or other container, but might also include one or more components such as wicks, capillary tubes, eminator pads, sealed chambers, and the like.

Regardless of the type of volatizable material used, the material delivery system may employ any form of controller to modulate the delivery of vapor into the environment. To the extent that the rate at which the vapor is introduced into the environment is a function of both the temperature of the volatizable material and the environmental convection conditions in the vicinity of the volatizable material, any suitable control mechanism may be employed to modulate these two factors. For example, the convection conditions may be controlled through the use of adjustable convection inhibitors (e.g., one or more vents) one or more convection enhancers (e.g., fans, chimney structures, etc.), or other structures that modify the vapor pressure in and around the material delivery system. Similarly, the temperature of the volatizable material and/or the temperature of the environment in the vicinity of the material delivery system may be controlled through any convenient method, including resistive heating (described above), or through proximity of the device to a preexisting heat source.

Notwithstanding the nature of receptacle 120—i.e., whether and to what extent receptacle 120 is configured to supply electrical current—delivery device 210 may be passive, active, or selectably switched between active and passive modes. The term "passive" in this context, as applied to delivery devices, refers to those devices which substantially depend upon ambient conditions to deliver a fragrance or otherwise give rise to a modification of the environment. Such ambient conditions include, for example, ambient thermal conditions (e.g., wall surface temperature and air temperature) and ambient air flow, (e.g., air flow resulting from free convection as well as the movement (if any) of fans, individuals, and other entities within the environment) .The term "active" in this context refers to devices that are not passive, e.g., devices which employ integrated fans, heating elements, and other such devices.

In the event that delivery system 110 is an active device, any power source required by the device may be intrinsic to receptacle 120, e.g., the 120 V source of a standard wall outlet, or extrinsic to receptacle 120, e.g., supplied by a battery, solar cell, or other such device incorporated into or otherwise associated with delivery system 110. Alternatively, power may be supplied by a combination of intrinsic and extrinsic sources and/or may be incorporated into a refill component.

Delivery device 110 suitably includes one or more removeably attached refill components. That is, referring to FIGS. 11A–11C, it may be advantageous for delivery device 110 to include components that are integral to the delivery system itself as well as one or more refill components 1120 (or simply "refills") that can be replaced by the user. In the event delivery system 110 is an air freshener device, for example, a depleted refill component 1120 may removed from system 110 and replaced by a new refill containing fragrant oil, wax, gel, or the like. The refill suitably includes a refill body and a volatizable material provided therein.

In accordance with one aspect of the present invention, a refill component is provided which allows vapor-dispensing device to mimic an electrical receptacle. For example, a refill component comprising a refill body having a volatizable material provided therein may be configured to be inserted behind the front surface of the device such that it is substantially concealed by the front surface. In accordance with one aspect of the present invention, the refill has a perimeter that is encompassed by the perimeter of the housing.

Figures 11A, 11B, 11C:
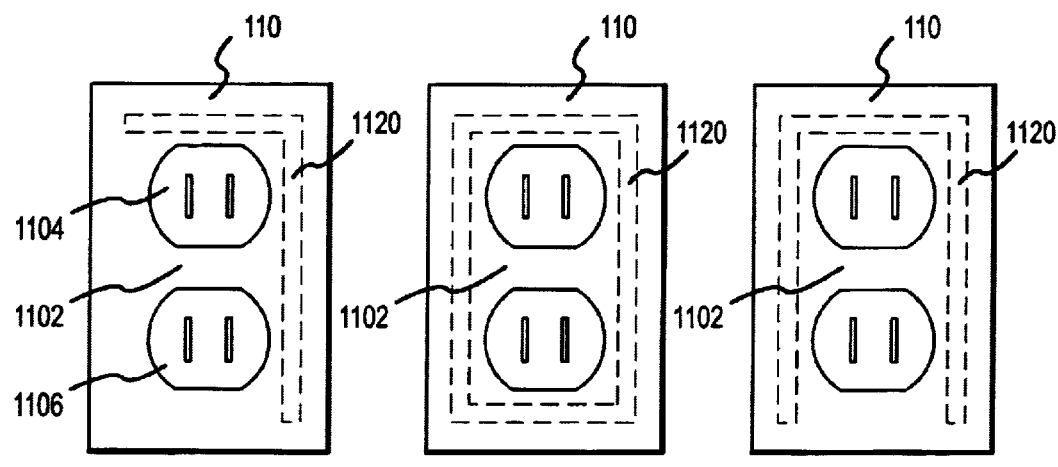
FIGS. 11A–11C show various refill configurations in accordance with the present invention.

In accordance with another aspect of the present invention, the refill is configured such that it does not significantly obstruct the receptacle's outlet pattern 1102 (comprising, for example, two outlets 1102 and 1104). In one embodiment, for example, this is accomplished by providing a refill component 1120 that at least partially surrounds one or more outlets on the receptacle (variously shown in FIGS. 11A–11C). In the event that the delivery device is used in connection with a standard electrical receptacle, it is desirable for refill 1120 to encompass two or more sides of the outlet pattern 1102 (FIG. 11A). To the extent that it is advantageous to supply the greatest possible volume of volatizable material, the refill may be configured as a rectangular ring that completely surrounds the outlet pattern 504 (FIG. 11B). Alternatively, the refill may be configured in a 'U' shape to allow refill 1120 to be slideably removed from the device (FIG. 11C).

Although the invention has been described herein in conjunction with the appended drawings, those skilled in the art will appreciate that the scope of the invention is not so limited. Modifications in the selection, design, and arrangement of the various components and steps discussed herein may be made without departing from the scope of the invention.

What is claimed is:

1. A refill component for use in connection with a vapor-dispensing device of the type configured to connect to an outlet having an outlet pattern, said refill component comprising:

a refill body configured to removeably attach to the vapor-dispensing device, said refill body configured to encompass at least two sides of the outlet pattern;

a volatizable material provided within said refill body;

at least one wicking structure substantially encapsulated by said refill body and communicating with said volatizable material;

an eminator coupled to said at least one wicking structure;

said volatizable material, said at least one wicking structure, and said eminator configured to interface with the vapor-dispensing to produce a range of evaporation rates corresponding to a range of sensory fragrance intensity values that span at least three minimum perceivable intensity zones for said volatizable material.

2. The refill component of claim 1, wherein said volatizable material comprises an oil-based liquid, and wherein said refill body further includes at least one wicking structure.

3. The refill component of claim 1, wherein said refill body is generally "U"-shaped, and wherein aid refill body further includes at least two wicking structures and at least one eminator.

* * * * *